United States Patent
Kawakubo

(10) Patent No.: US 8,724,858 B2
(45) Date of Patent: May 13, 2014

(54) DRIVER IMAGING APPARATUS AND DRIVER IMAGING METHOD

(75) Inventor: Atsushi Kawakubo, Toyota (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 603 days.

(21) Appl. No.: 12/681,009

(22) PCT Filed: Mar. 11, 2009

(86) PCT No.: PCT/IB2009/000483
§ 371 (c)(1),
(2), (4) Date: Mar. 31, 2010

(87) PCT Pub. No.: WO2009/138828
PCT Pub. Date: Nov. 19, 2009

(65) Prior Publication Data
US 2010/0220892 A1 Sep. 2, 2010

(30) Foreign Application Priority Data

May 12, 2008 (JP) ................................. 2008-125057

(51) Int. Cl.
*G06K 9/00* (2006.01)
(52) U.S. Cl.
USPC .......................................... 382/118; 382/117
(58) Field of Classification Search
USPC ................ 382/115, 117, 118; 340/5.53, 5.83; 348/78
See application file for complete search history.

(56) References Cited

U.S. PATENT DOCUMENTS

| 2004/0071318 A1 | 4/2004 | Cheung et al. |
| 2006/0259206 A1 | 11/2006 | Smith et al. |
| 2007/0014431 A1 | 1/2007 | Hammoud et al. |
| 2007/0291989 A1 | 12/2007 | Ito et al. |
| 2007/0292000 A1 | 12/2007 | Ito et al. |

FOREIGN PATENT DOCUMENTS

| EP | 1 723 901 | 11/2006 |
| EP | 1 732 028 | 12/2006 |
| JP | 8 101133 | 4/1996 |
| JP | 9-21611 | 1/1997 |
| JP | 9 107499 | 4/1997 |
| JP | 3422183 | 4/2003 |
| JP | 2004 192345 | 7/2004 |
| JP | 2005-301742 | 10/2005 |
| JP | 2006-139701 | 6/2006 |
| JP | 2007-251558 | 9/2007 |
| JP | 2008-27242 | 2/2010 |

OTHER PUBLICATIONS

Office Action issued Mar. 29, 2010, in Japan Patent Application No. JP 2008-125057.

*Primary Examiner* — John Strege
(74) *Attorney, Agent, or Firm* — Oblon, Spivak, McClelland, Maier & Neustadt, L.L.P.

(57) ABSTRACT

An imaging mechanism captures an image of a face of a driver of a vehicle. A first image processor performs image processing on a wide portion of the face of the driver in a first image using a first image captured by the imaging mechanism. A second image processor performs image processing on a part of the face of the driver in a second image captured by the imaging mechanism at a higher exposure than the exposure of the first image, using the second image.

21 Claims, 5 Drawing Sheets

DRIVER IMAGING APPARATUS AND DRIVER IMAGING METHOD

BACKGROUND OF THE INVENTION

1. Field of the Invention

The invention relates to a driver imaging apparatus and a driver imaging method for capturing an image of a driver in a vehicle from the front.

2. Description of the Related Art

Systems are under development which capture an image of a driver driving a vehicle and monitor the state of the driver using the captured image. For example, a camera for capturing an image of the driver from the front is arranged near a steering wheel of the vehicle and the state of the driver is analyzed using the image captured by the camera.

Japanese Patent Application Publication No. 2004-192345, for example, describes a driver state detecting apparatus which determines the degree to which the eyes of the driver are open (hereinafter also referred to as "eye opening degree") and the direction in which the driver is gazing (i.e., hereinafter also referred to as "direction of gaze") using an image of the driver. The driver state detecting apparatus described in that publication detects a coordinate value of the eyes of the driver from the image. Then the driver state detecting apparatus determines the direction of gaze of the driver or the degree to which the eyes of the driver are open to determine whether the driver is inattentive or nodding off.

However, when capturing an image of the driver in the vehicle from the front, light from outside the vehicle may produce a shadow around the eyes of the driver, causing that area to appear dark, and thus lack contrast, in the image, i.e., resulting in a dark (i.e., underexposed) image. In this case, the degree to which the eyes of the driver are open and the position of the eyes are unable to be detected so it is difficult to determine the degree to which the eyes of the driver are open or the direction of gaze of the driver.

To prevent this, it is possible to increase the amount of exposure (simply referred to as "exposure" in this specification) when capturing the image of the driver (e.g., increase the electronic shutter time) so as to increase the amount of light on the shadowed portion in order to prevent that portion from being underexposed. However, when the exposure is determined using the area near the eyes of the driver that are in a shadow as the reference, an image in which the area near the eyes is light is able to be obtained but contrast in other light portions such as the outline of the face of the driver is lost (i.e., overexposed). As a result, processing using the image of that light portion is unable to be performed.

SUMMARY OF THE INVENTION

This invention thus provides a driver imaging apparatus and a driver imaging method capable of capturing an image suitable for determining the state of a driver, and determining the state of the driver.

A first aspect of the invention relates to a driver imaging apparatus that includes: imaging means for capturing an image of a face of a driver of a vehicle; first image processing means for performing image processing on a wide portion of the face of the driver in a first image captured by the imaging means, using the first image; and second image processing means for performing image processing on a part of the face of the driver in a second image captured by the imaging means at a higher exposure than the exposure of the first image captured by the imaging means, using the second image.

According to this aspect, image processing using portions where appropriate contrast can be obtained in each of a plurality of images captured at different exposures is possible so the state of the driver can be accurately determined. For example, the state of the driver can be accurately determined by performing image processing of a wide portion of the face of the driver that appears light, using the first image (i.e., the image captured at a relatively low exposure), and performing image processing of a part of the face of the driver that appears dark, using the second image (i.e., the image captured at a relatively high exposure).

In the aspect described above, the second image processing means may detect at least one of i) the degree to which the eyes of the driver are open or ii) the direction in which the driver is gazing, by performing image processing on a portion around the eyes of the driver in the second image.

According to this structure, the eye opening degree and the direction of gaze are detected by performing image processing on a part of the face such as the area around the eyes of the driver that appears dark, using the second image.

In the structure described above, the second image processing means may detect at least one of i) the degree to which the eyes of the driver are open or ii) the direction in which the driver is gazing, by performing image processing on the mouth, eyebrows, and wrinkles of the driver in the second image.

In the structure described above, the first image processing means may detect at least one of i) the direction in which the face of the driver is pointed with the front of the vehicle as a reference or ii) the position of the eyes of the driver, by performing image processing on a wide portion of the face of the driver in the first image.

According to this structure, the direction in which the face of the driver is pointed and the position of the eyes of the driver are determined by performing image processing of the wide portion (such as the outline, the nostrils, and the like) of the face of the driver that appear light, using the first image. As a result, it is possible to make a determination (such as a determination as to whether the driver is being inattentive based on the direction in which the face of the driver is pointing) based on the state of the wide portion of the face of the driver using an image captured at a relatively low exposure with respect to portions that appear light. As a result, the state of the driver can be accurately determined based on the state of that portion.

In the structure described above, the first image processing means may detect an area where the eyes of the driver are in the first image, by performing image processing on the wide portion of the face of the driver in the first image. Also, the second image processing means may detect at least one of i) the degree to which the eyes of the driver are open or ii) the direction in which the driver is gazing, by performing image processing on the second image in the area detected by the first image processing means.

According to this structure, the area where the eyes are in the image can be detected using the first image in which contrast in the wide portion (the outline, the nostrils, and the like) of the face of the driver can be obtained. Therefore, that area can be accurately determined. Also, the degree to which the eyes of the driver are open and the direction in which the driver is gazing can be detected by performing image processing to search that area using the second image in which contrast in a part of the face such as the area around the eyes of the driver can be obtained. Therefore, the search range in the image processing can be reduced and the state of the eyes of the driver can be accurately determined.

The driver imaging apparatus described above may also include shutter controlling means for controlling a shutter time which is the period of time during which light is taken in while the imaging means is capturing an image. The shutter controlling means may control the exposure when the imaging means captures an image by making the shutter time when the second image is captured relatively long compared to the shutter time when the first image is captured.

According to this structure, first and second images which are captured at different exposures can easily be obtained by adjusting the shutter time of the imaging means (such as the electronic shutter time of a CCD, for example).

In the structure described above, the shutter controlling means may include shutter time correcting means for correcting the shutter time when the first image is captured according to the brightness of the wide portion in the first image, and correcting the shutter time when the second image is captured according to the brightness of the part in the second image.

According to this structure, the brightness of the captured object can be adjusted appropriately for the portion on which image processing is to be performed, by correcting the shutter time for capturing the first image according to the brightness of the wide portion of the face of the driver, and correcting the shutter time for obtaining the second image according to the brightness of a part of the face of the driver. Therefore, processing using an image in which contrast in the portion that is to undergo image processing can be suitably obtained is always possible.

The driver imaging apparatus described above may also include aperture controlling means for controlling the opening amount of an aperture that allows light into the imaging means. The aperture controlling means may control the exposure when the imaging means captures an image by making the opening amount of the aperture when the second image is captured relatively large compared to the opening amount of the aperture when the first image is captured.

In the structure described above, the aperture controlling means may include aperture opening amount correcting means for correcting the opening amount of the aperture when the first image is captured according to the brightness of the wide portion in the first image, and correcting the opening amount of the aperture when the second image is captured according to the brightness of the part in the second image.

The driver imaging apparatus described above may also include photosensitivity controlling means for controlling the photosensitivity of the imaging means. The photosensitivity controlling means may control the exposure when the imaging means captures an image by making the photosensitivity when the second image is captured higher than the photosensitivity when the first image is captured.

In the structure described above, the photosensitivity controlling means may include photosensitivity correcting means for correcting the photosensitivity when the first image is captured according to the brightness of the wide portion in the first image, and correcting the photosensitivity when the second image is captured according to the brightness of the part in the second image.

The driver imaging apparatus described above may also include exposure controlling means for controlling the exposures when the imaging means captures the images. The exposure controlling means may cyclically alternate the timing at which the imaging means captures an image with the exposure at which the first image is captured with the timing at which the imaging means captures an image with the exposure at which the second image is captured.

According to this structure, a first image and a second image that are captured at close timings are able to be obtained by capturing the first image and the second image alternately in cycles so it is possible to determine the state of the driver that has been captured in substantially the same position and state.

In the structure described above, the first image processing by the first image processing means may be performed at a separate timing than the second image processing by the second image processing means.

The driver imaging apparatus described above may also include storing means for storing the first image and the second image. The first image processing means and the second processing means may each perform image processing using a combination of the first image and the second image captured in succession and stored in the storing means.

In the structure described above, the position of the eyes of the driver may be identified by detecting the position of the nose of the driver.

A second aspect of the invention relates to a driver imaging apparatus that includes: imaging means for capturing an image of a face of a driver of a vehicle; face direction determining means for determining the direction in which the face of the driver is pointed in a first image captured by the imaging means with the front of the vehicle as a reference, using the first image; and eye information detecting means for i) determining the degree to which the eyes of the driver are open in a second image, which is captured by the imaging means at a higher exposure than the exposure of the first image captured by the imaging means, using the second image, or ii) determining the direction in which the driver is gazing in the second image, which is captured by the imaging means at a higher exposure than the exposure of the first image captured by the imaging means, using the second image.

According to this aspect, image processing using portions where appropriate contrast can be obtained in each of a plurality of images captured at different exposures is possible so the direction in which the face of the driver is pointed and the degree to which the eyes of the driver are open can be accurately determined.

A third aspect of the invention relates to a driver imaging method that includes: performing image processing on a wide portion of a face of a driver of a vehicle in a first image, in which the face of the driver is captured, using the first image; and performing image processing on a part of the face of the driver in a second image, in which the face of the driver is captured at a higher exposure than the exposure of the first image, using the second image.

A fourth aspect of the invention relates to a driver imaging method that includes: determining the direction in which a face of a driver of a vehicle is pointed in a first image, in which the face of the driver is captured, with the front of the vehicle as a reference, using the first image; and determining the degree to which the eyes of the driver are open in a second image, in which the face of the driver is captured at a higher exposure than the exposure of the first image, using the second image, or determining the direction in which the driver is gazing in the second image, in which the face of the driver is captured at a higher exposure than the exposure of the first image, using the second image.

Also, the driver imaging method of the invention is also able to yield the same effects as those yielded by the driver imaging apparatus described above.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein.

DETAILED DESCRIPTION OF AN EMBODIMENT

A driver imaging apparatus according to an example, embodiment of the invention will now be described with reference to FIG. 1. Incidentally, in this example embodiment, a driver support system that includes the driver imaging apparatus is provided in a vehicle. As an example, the driver support system captures an image of the face of a driver driving the vehicle, determines the state of the driver (e.g., the direction in which the driver is facing, the eye opening degree, and the direction of gaze, and the like) based on the image, and controls the vehicle according to the determination results. Also, the driver support system also recognizes other vehicles and obstacles around the vehicle, determines the risk of collision, and controls the vehicle according to the determination results. Incidentally, FIG. 1 is a block view of an example of the functional structure of the driver support system that includes the driver imaging apparatus.

Figure 1:
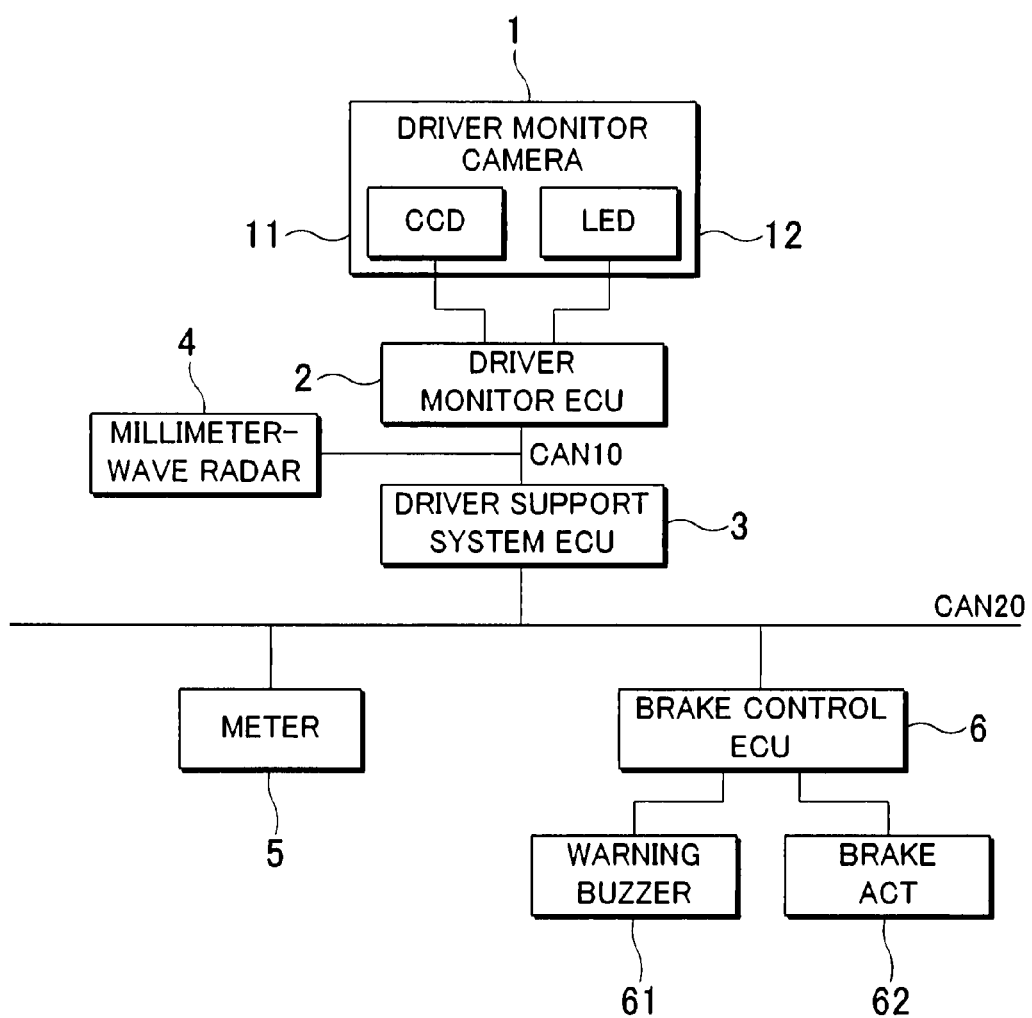
FIG. 1 is a block diagram of an example of the functional structure of a driver support system that includes a driver imaging apparatus according to an example embodiment of the invention.

Referring to FIG. 1, the driver support system includes a driver monitor camera 1, a driver monitor ECU (Electronic Control Unit) 2, a driver support system ECU 3, a millimeter-wave radar 4, a meter 5, a brake control ECU 6, a warning buzzer 61, and a brake actuator 62. The driver monitor ECU 2, the driver support system ECU 3, and the millimeter-wave radar 4 are all connected together via a CAN (Controller Area Network) 10 and the like. Also, the driver support system ECU 3, the meter 5, and the brake control ECU 6 are all connected together via a CAN 20 and the like.

The driver monitor camera 1 includes a CCD (Charge Coupled Device) 11 and a LED (Light Emitting Diode) 12 which each operate using power from the driver monitor ECU 2. For example, the LED 12 emits near-infrared light toward the driver from in front of the driver. In this case, the CCD 11 is an imaging device that is highly sensitive in the near-infrared region, and is typically a near-infrared CCD camera. In this way, by using the CCD 11 that is highly sensitive in the near-infrared region, an image of the driver that is illuminated by the LED 12 can be captured with good sensitivity even when it is dark inside the vehicle while driving at night or in a tunnel or the like. Incidentally, the CCD 11 is mounted in a position where it can capture an image of the face of the driver from the front. The CCD 11 captures an image of the face of the driver and the area therearound at predetermined cycles and outputs the captured image to the driver monitor ECU 2. More specifically, the CCD 11 alternately captures two images with different exposure (i.e., a first image P1 and a second image P2) according to instructions from the driver monitor ECU 2 in predetermined cycles, and outputs the two captured images to the driver monitor ECU 2. Incidentally, the position in which the driver monitor camera 1 is mounted will be described in detail later.

The driver monitor ECU 2 is a processing unit that includes a plurality of information processing devices such as microcomputers inside it, memory that stores various types of information used for processing, a power supply circuit for supplying power to the driver monitor camera 1, and an interface circuit and the like. For example, the driver monitor ECU 2 uses the image captured by the driver monitor camera 1 to detect the direction in which the driver is facing, the degree to which the eyes of the driver are open, and the direction of gaze. The driver monitor ECU 2 outputs the detection results to the driver support system ECU 3. Also, the driver monitor ECU 2 adjusts the exposure of the image captured by the CCD 11 using the two images that are alternately captured in predetermined cycles.

The millimeter-wave radar 4 emits a millimeter wave in front of the vehicle, in back of the vehicle, or diagonally in front of the vehicle or the like and receives the radio waves reflected off of an object. Then the millimeter-wave radar 4 measures the position of an obstacle or another vehicle around the vehicle, as well as the relative speed between the vehicle and the other vehicle or obstacle, and outputs the results to the driver support system ECU 3.

The driver support system ECU 3 appropriately adjusts the characteristics of an occupant protection apparatus in the vehicle, operates a collision avoidance/mitigation system, and issues an appropriate warning to the driver, based on the information related to the direction in which the driver is facing, the degree to which the eyes of the driver are open, and the direction in which the driver is gazing and the like, as well as the recognition results with respect to a vehicle or obstacle around the vehicle which are output from the millimeter-wave radar 4. The meter 5 and the brake control ECU 6 in FIG. 1 are examples of devices controlled by the driver support system ECU 3.

The meter 5 is provided near the driver's seat in the vehicle, in a position visible by the driver that is driving the vehicle. For example, the meter 5 is provided on an instrument panel in front of the driver and displays a warning to the driver according to a command from the driver support system ECU 3. For example, if it is determined that the driver is not looking forward, is closing his or her eyes, or is inattentive such that there is a risk of the vehicle colliding with another object, the driver support system ECU 3 promptly illuminates a display on the meter 5 prompting the driver to take action to avoid a collision (i.e., issues an early warning). Typically, the meter 5 is formed by a combination display or the like in which several main gauges, indicator lights, warning lights, and multiple information displays that display various information and the like are combined in one panel. Incidentally, the meter 5 may also be formed by another display device such as a Head-Up Display in which a half mirror (reflective glass) is provided on a portion of the front windshield in front of the driver's seat and a virtual image of information or the like is displayed in fluorescent on the half mirror.

The brake control ECU 6 controls the operation of the warning buzzer 61 and the brake actuator 62 provided in the vehicle. For example, if the driver support system ECU 3 determines that the driver is not looking forward, is closing his or her eyes, or is inattentive such that there is a risk of the vehicle colliding with another object, the brake control ECU 6 promptly activates the warning buzzer 61 to prompt the driver to take action to avoid a collision (i.e., issues an early warning). As a result, the driver can promptly take action to avoid a collision by paying attention for example. Also, the brake control ECU 6 controls the operation of the brake actuator 62 to assist with increasing the brake pressure according to the force with which the driver depresses the brake pedal (i.e., performs warning braking). As a result, the hydraulic pressure response of the brake actuator 62 improves so the speed of the vehicle can be reduced.

Figure 2:
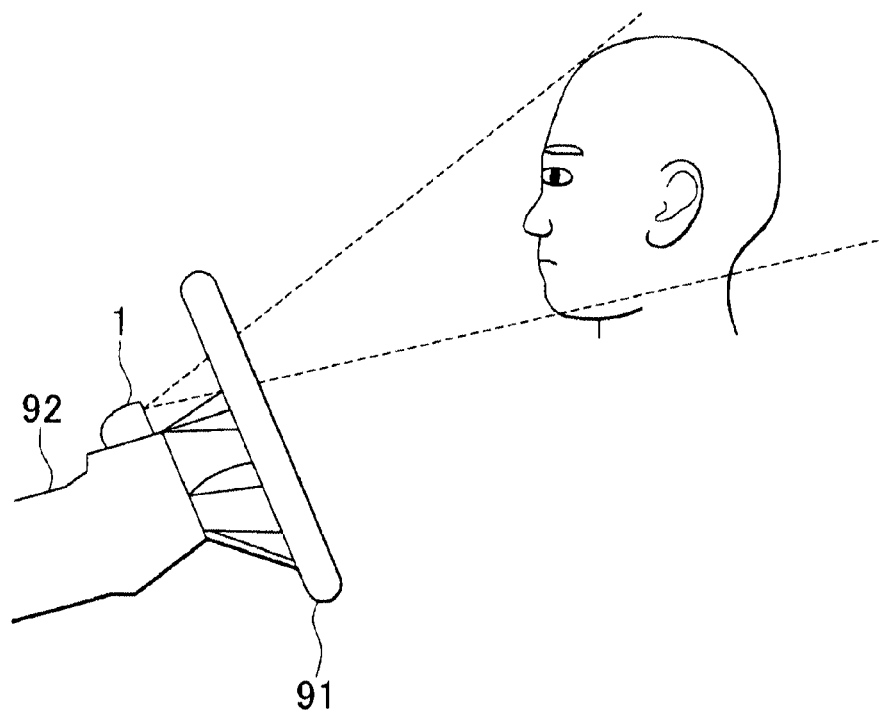
FIG. 2 is a side view schematically showing an example of a driver monitor camera mounted in a vehicle as viewed from the side of the driver's seat.
Figure 3:
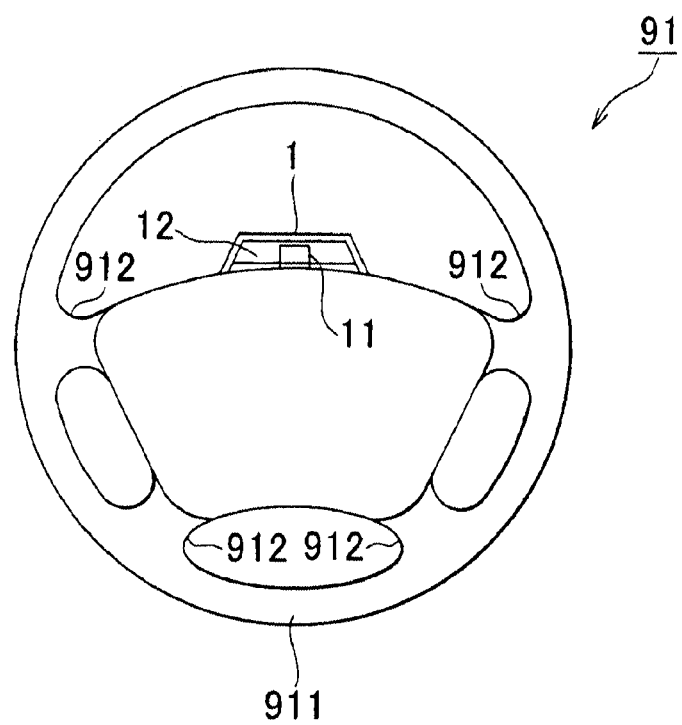
FIG. 3 is a front view schematically showing an example of the driver monitor camera mounted in the vehicle as viewed from the steering wheel side.

Next, the driver monitor camera 3 will be described with reference to FIGS. 2 and 3. Incidentally, FIG. 2 is a side view schematically showing an example of the driver monitor camera 1 mounted in the vehicle as viewed from the side of the driver's seat. FIG. 3 is a front view schematically showing an example of the driver monitor camera 1 mounted in the vehicle as viewed from a steering wheel 91 side.

In FIGS. 2 and 3, the driver monitor camera 1 is mounted on a steering column 92. The CCD 11 of the driver monitor camera 1 adjusts the imaging direction so that an image can be taken of the face of the driver that is operating the steering wheel 91, from in front of the driver through an opening in the steering wheel 91 (such as an opening where there are no spokes 912 or the like on the inside of a rim 911. Incidentally, in FIG. 2, the portion of the surveillance area showing the field of view of the CCD 11 (a portion of the angle of view of the camera) is shown by the broken line. The imaging direction of the CCD 11 is adjusted so that the head of the driver is within the surveillance area. In this case, the LED 12 is provided in the driver monitor camera 1 as described above. The LED 12 emits near-infrared light toward the driver from in front of the driver in the same direction as the imaging direction. Incidentally, the LED 12 emits this near-infrared light at least over an area that is wider than the angle of view of the driver monitor camera 1. As described above, the driver monitor camera 1 is mounted on the steering column 92 so it can capture an image of the driver from a close distance in front of the driver, thus enabling an image of the face of the driver in the vehicle to be captured accurately.

Next, the first image P1 and the second image P2 which are captured by the driver monitor camera 1 will be described with reference to FIGS. 4 and 5. Incidentally, FIG. 4 is a view of an example of the first image of the driver captured by the driver monitor camera 1 at a relatively low exposure (i.e., with a relatively small amount of exposure), and FIG. 5 is a view of an example of the second image of the driver captured by the driver monitor camera 1 at a relatively high exposure (i.e., with a relatively large amount of exposure).

Figure 4:
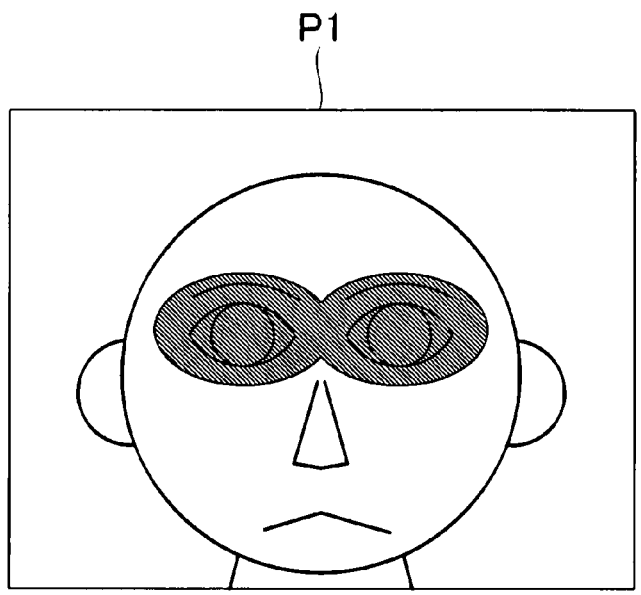
FIG. 4 is a view of an example of a first image of a driver captured by the driver monitor camera with a relatively low exposure.

In FIG. 4, when the driver monitor camera 1 captures an image of the driver, the image is generally captured at an exposure that corresponds to the brightness of the overall face of the driver (the image obtained at this time is designated as the first image P1). Therefore, in the first image P1, light from outside the vehicle, for example, may produce a shadow around the eyes of the driver, causing that area to appear dark, and thus lack contrast (due to underexposure), in the image as shown by the hatched area in FIG. 4. In particular, when there are a lot of lines and curves on the face, these lines and curves create shadows which often appear as dark portions in the image. However, in the first image P1, contrast in the light portions of the overall face of the driver can be obtained so this first image P1 is suitable for detecting wide portions such as the outline and position of the nostrils and the like of the face of the driver.

Figure 5:
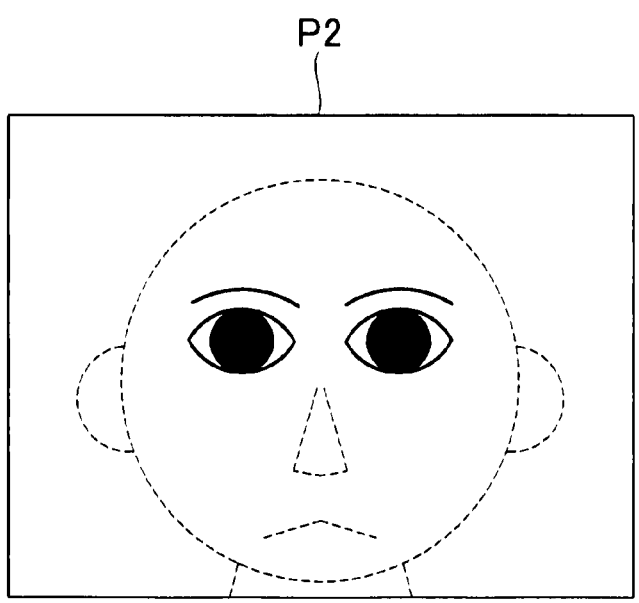
FIG. 5 is a view of an example of a second image of the driver captured by the driver monitor camera with a relatively high exposure.

In FIG. 5, when the driver monitor camera 1 captures an image of the driver at a relatively high exposure (such as when the electronic shutter time is long), the dark portions described above are lightened (the image obtained at this time is designated as the first image P2). Therefore, in the second image P2, contrast in the portions that would appear dark with a typical exposure is able to be obtained so this second image P2 is suitable for image processing with respect to parts of the face such as the eyes of the driver. However, second image P2 may lack contrast (due to overexposure) in the light parts of the overall face of the driver (as shown by the broken lines in FIG. 5).

The driver imaging apparatus according to this example embodiment performs image processing on the wide portions of the face of the driver (such as the outline of the face and the position of the nostrils) using the image with relatively low exposure, i.e., the first image P1. The driver imaging apparatus also performs image processing on the parts of the face of the driver (such as the eyes) using the image with relatively high exposure, i.e., the second image P2.

Figure 6:
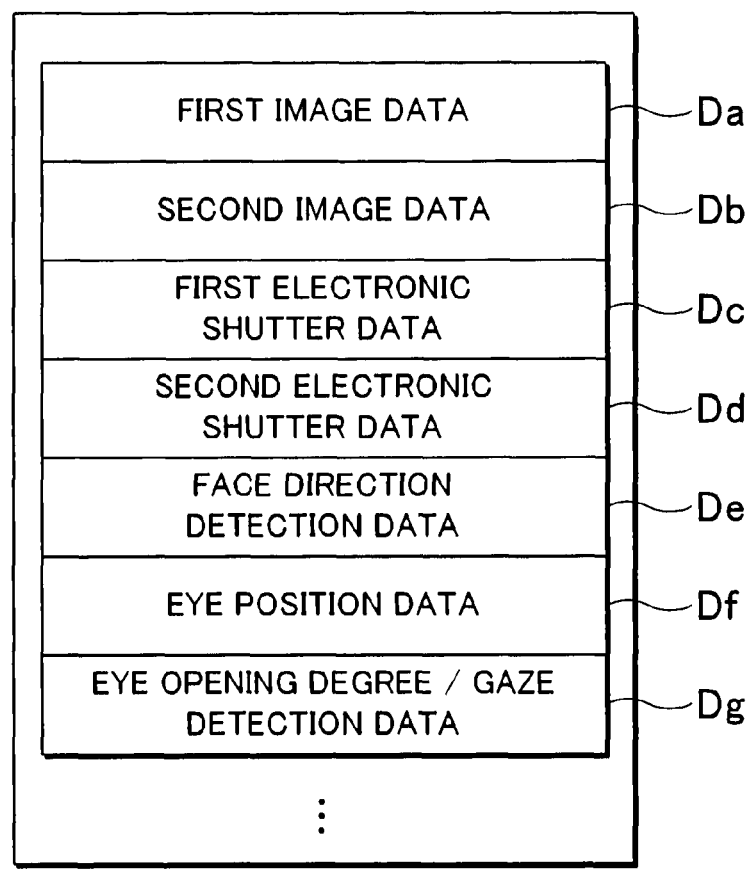
FIG. 6 is an example of main data stored in the memory of a driver monitor ECU.
Figure 7:
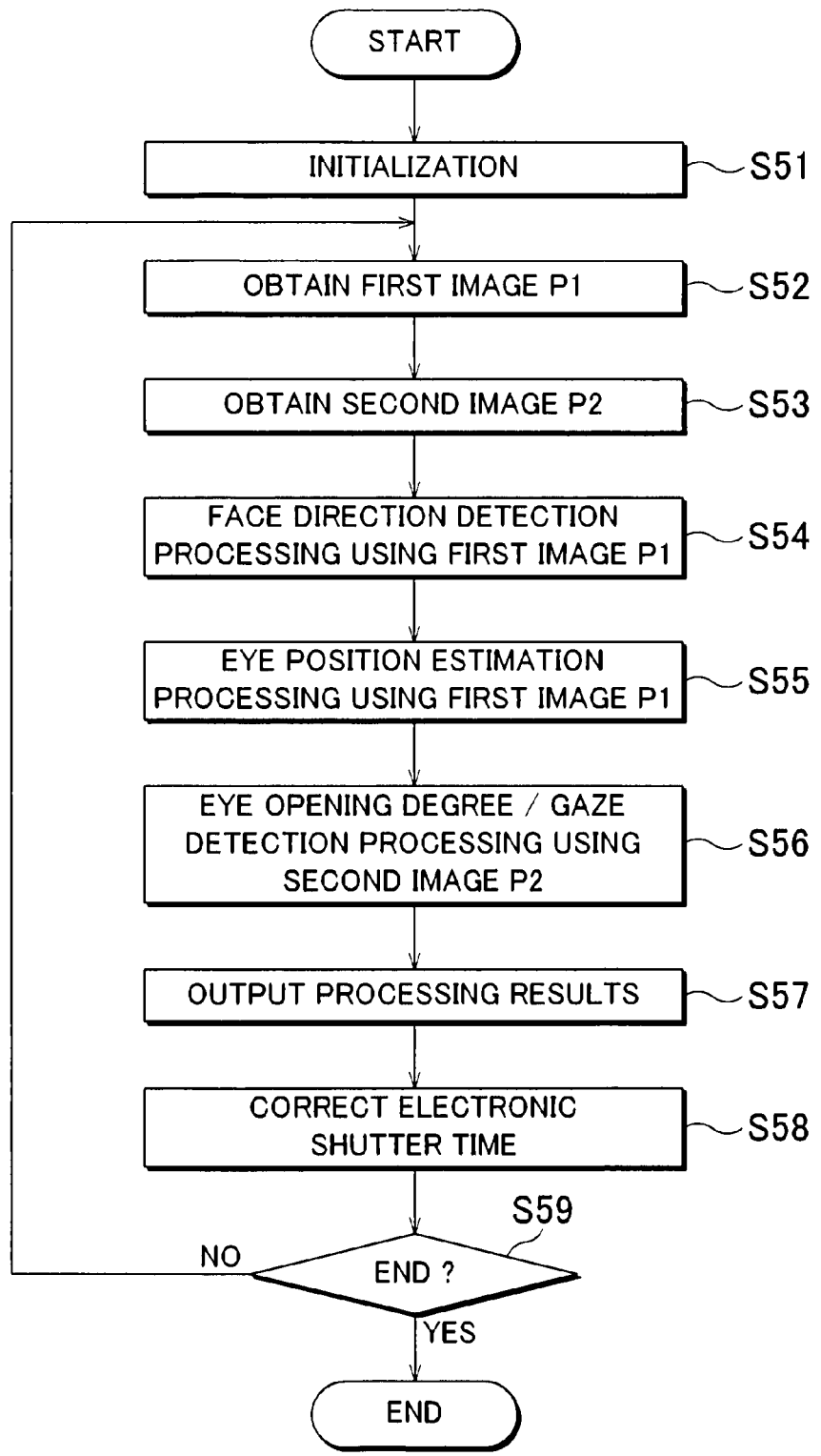
FIG. 7 is a flowchart illustrating an example of a routine executed by the driver monitor ECU.

Next, an example of the main data used in the driver image processing and the operation of the driver monitor ECU 2 will be described with reference to FIGS. 6 and 7. Incidentally, FIG. 6 is an example of the main data stored in the memory of the driver monitor ECU 2, and FIG. 7 is a flowchart illustrating an example of a routine executed by the driver monitor ECU 2. Also, the steps in the flowchart shown in FIG. 7 are performed by the driver monitor ECU 2 executing a predetermined program. The program for executing these steps is stored in advance in a storage area (such as memory, a hard disk, an optical disk or the like) provided in the driver monitor ECU 2, and is executed by the driver monitor ECU 2 when the power supply of the driver monitor 2 is on, for example.

In FIG. 6, first image data Da, second image data Db, first electronic shutter data Dc, second electronic shutter data Dd, face direction detection data De, eye position data Df, and eye opening degree/gaze detection data Dg, and the like are stored in the memory of the driver monitor ECU 2.

The first image data Da is stored data which is indicative of the image captured at a relatively low exposure by the driver monitor camera 1, i.e., the first image P1, and is updated at predetermined processing cycles. The second image data Db is stored data which is indicative of the image captured at a relatively high exposure by the driver monitor camera 1, i.e., the second image P2, and is updated at predetermined processing cycles. Incidentally, as will be described later, the time difference between the timing at which the first image P1 to be stored as the first image data Da is captured and the timing at which the second image P2 to be stored as the second image data Db is captured is an extremely short time interval (i.e., the interval between imaging cycles of the driver monitor camera 1, such as $\frac{1}{30}$ or $\frac{1}{60}$ of a second).

The first electronic shutter data Dc is stored data which is indicative of the electronic shutter time (i.e., the light-gathering time) when the driver monitor camera 1 captures the first image P1. The second electronic shutter data Dd is stored data which is indicative of the electronic shutter time when the driver monitor camera 1 captures the second image P2.

The face direction detection data De is stored data which is indicative of the face angle α that indicates the angle at which the face of the driver is turned to the left or the right with respect to the front. The eye position data Df is stored data which is indicative of the position and size of a left eye search range and a right eye search range set for the first image P1. The eye opening degree/gaze detection data Dg is stored data which is indicative of the degree to which the eyes of the driver are open as well as the direction in which the driver is gazing.

Next, a predetermined program executed by the driver monitor ECU 2 will be described with reference to FIG. 7. First, the driver monitor ECU 2 performs initialization in step S51 and then proceeds on to the next step. More specifically, in step S51, the driver monitor ECU 2 initializes the parameters and image data and the like stored in the memory. For example, the driver monitor ECU 2 sets the electronic shutter time when capturing the first image P1 and the electronic shutter time when capturing the second image P2 to predetermined default times, and stores the first image P1 as the first electronic shutter data Dc and the second image P2 as the second electronic shutter data Dd using these times.

Next in step S52, the driver monitor ECU 2 obtains the first image P1 from the driver monitor camera 1 and updates the first image data Da, after which it proceeds on to the next step. For example, the driver monitor ECU 2 obtains the electronic shutter time for the first image P1 referencing the first electronic shutter data Dc, and controls the operation of the driver monitor camera 1 to capture an image with that electronic shutter time. Then the driver monitor ECU 2 obtains data indicative of the first image P1 captured with the electronic shutter time for the first image P1 from the driver monitor camera 1 and updates the first image data Da.

Next in step S53, the driver monitor ECU 2 obtains the second image P2 from the driver monitor camera 1 and updates the second image data Da, after which it proceeds on to the next step. For example, the driver monitor ECU 2 obtains the electronic shutter time for the second image P2 referencing the second electronic shutter data Dd and controls the operation of the driver monitor camera 1 to capture an image with that electronic shutter time. Then the driver monitor ECU 2 obtains data indicative of the second image P2 captured with the electronic shutter time for the second image P2 from the driver monitor camera 1 and updates the second image data Db.

Here, the processing interval between steps S52 and S53 is preferably as short as possible. For example, when the imaging cycle of the driver monitor camera 1 is 30 or 60 frames per second, the processing interval between steps S52 and S53 may be 1/30 or 1/60 of a second to match the imaging cycle. As a result, the difference between the timing at which the first image P1 to be stored as the first image data Da is captured and the timing at which the second image P2 to be stored as the second image data Dd is captured can be made extremely short.

Next in step S54, the driver monitor ECU 2 uses the first image P1 to perform face direction detection processing to detect how far the face of the driver is turned to the left or right with respect to forward, after which it proceeds on to the next step. Hereinafter, an example of this face direction detection processing performed in step S54 will be described.

For example, the driver monitor ECU 2 calculates a face angle α indicative of how far the face of the driver is turned toward the left or right with respect to the front of the vehicle, based on the first image P1 obtained in step S52 described above. In this case, the value of the face angle α is 0 when the driver is facing forward (i.e., toward the front of the vehicle) with respect to the camera 1. The value of the face angle α increases as the face turns from the front with respect to the driver monitor camera 1 farther to the right, and decreases as the face turns from the front with respect to the driver monitor camera 1 farther to the left. That is, the value of the face angle α is a positive value when the face is turned toward the right with respect to the driver monitor camera 1 and is a negative value when the face is turned toward the left with respect to the driver monitor camera 1.

The driver monitor ECU 2 detects the left and right outline edges of the face of the driver and a vertical centerline of the face in the image P1 by searching for the outline of the face and a vertical centerline which is the center in the left-right direction of the face in the first image P1 according to edge extraction processing using a Sobel operator or the like. For example, the driver monitor ECU 2 creates a bright image of the first image P1 and applies edge extraction processing to that bright image to extract the positions of the left and right outline edges of the face and parts of the face (e.g., eyebrows, eyes, nose, and mouth). Next, the driver monitor ECU 2 calculates the width of the face and the vertical centerline in the first image P1 based on the extracted positions of the left and right outline edges of the face and parts of the face. Then the driver monitor ECU 2 calculates the width of the left half of the face from the left outline edge to the vertical centerline (also referred to as "left-face width" in the specification), as well as the width of the right half of the face from the right outline edge to the vertical centerline (also referred to as "right-face width" in the specification).

Next, the driver monitor ECU 2 calculates the face angle α based on the ratio of the values of the left-face width and the right-face width. For example, when the face of the driver is facing forward with respect to the driver monitor camera 1, the right-face width and the left-face width are equal. However, when the face of the driver is turned to the right, the left-face width is greater than the right-face width. That is, the ratio of the right-face width and the left-face width changes according to the face angle α. Therefore, the driver monitor ECU 2 calculates the face angle α based on the ratio of the right-face width and the left-face width. Also, the driver monitor ECU 2 updates the face direction detection data De using the data indicative of the calculated face angle α.

In this way, the face direction detection processing performed in step S54 is performed using the first image P1. In this case, in the first image P1 described above, contrast in the light portions of the overall face of the driver can be obtained so this first image P1 is suitable for detecting the position of the nostrils and the like as well as the outline of the face of the driver. In the face direction detection processing described above, the peripheral portions of the face and the vertical center line of the face in the image are found through edge extraction processing so an accurate face angle α can be obtained using the first image P1.

After face direction detection processing is performed in step S54, the driver monitor ECU 2 performs eye position estimation processing to estimate where the area in which the eyes of the driver are positioned is using the first image P1 in step S55, and then proceeds on to the next step. Hereinafter, an example of this eye position estimation processing performed in step S55 will be described.

First, the driver monitor ECU 2 sets the area where it is estimated that an image of the nose of the driver will be in the first image P1 using the information regarding the width of the face of the driver calculated in step S54 and the like. Then the driver monitor ECU 2 searches the portion with the nose of the driver within that area, and detects the position of the nose in the first image P1. Mores specifically, the driver monitor ECU 2 detects the position of both nostrils within that area. Then the driver monitor ECU 2 sets the position in the center between the nostrils as the position of the nose in the first image P1. Incidentally, there is typically less difference in the shape of the nostrils than there is in the eyes and the like so the position of the nostrils is able to be detected more accurately than the position of the eyes and the like.

Next, the driver monitor ECU 2 sets the optimal left eye search range and the optimal right eye search range using the position of the nose as a reference for the first image P1. For example, the driver monitor ECU 2 sets the left eye search range and the right eye search range to positions in the first image P1 that is a predetermined distance away in a predetermined direction from the position of the nose. In this case, the direction and distance where the left and right eye search ranges are set based on the position of the nose may be set based on predetermined reference information. Incidentally, the direction and distance where the left and right eye search ranges are set and the size of the left and right eye search ranges may also be changed. As a result, even if the size of the face of the driver in the first image P1 changes (i.e., typically, even if the distance between the face of the driver and the driver monitor camera 1 changes) the position and size of the left and right eye search ranges may be appropriately set to follow the change in the size of the face. Then the driver monitor ECU 2 updates the eye position data Df using the data indicative of the position and size of the set left and right eye search ranges.

In this way, the eye position estimation processing performed in step S55 is performed using the first image P1. In this case, just as described above, in the first image P1, contrast in the light portions of the overall face of the driver can be obtained so this first image P1 is suitable for detecting the position of the nostrils and the like of the driver. In the eye position estimation processing, the position of the left eye search range and the right eye search range are set using the position of the nostrils of the face in the image as a reference so an accurate search range can be set using the first image P1.

After the eye position estimation processing performed in step S55, the driver monitor ECU 2 performs eye opening degree/gaze detection to detect the degree to which the eyes of the driver are open and the direction of gaze in step S56 using the second image P2, after which it proceeds on to the next step. Hereinafter, an example of this eye opening degree/gaze detection performed in step S56 will be described.

First, the driver monitor ECU 2 detects the positions of the left and right eyes in the second image P2. In this case, as described above, the first image P1 and the second image P2 are images captured by the same driver monitor camera 1 at extremely short time intervals. That is, it can be assumed that the object (i.e., the face of the driver) captured in the first image P1 and the second image P2 is captured in generally the same state and position. Also, data indicative of the positions and sizes of the left eye search range and the right eye search range set in the first image P1 is stored as the eye position data Df. Therefore, the driver monitor ECU 2 applies the positions and sizes of the left eye search range and the right eye search range set in the first image P1 as they are to the second image P2, and sets the left eye search range and the right eye search range for the second image P2.

Then the driver monitor ECU 2 searches for and detects the left eye of the driver within the left eye search range set in the second image P2 referencing the second image data Db. The driver monitor ECU 2 also searches for and detects the right eye of the driver within the right eye search range set in the second image P2. For example, the eyes can be detected in the search ranges using any of various pattern matching methods that use a template image of the eyes set beforehand.

Next, the driver monitor ECU 2 calculates the degree to which both eyes of the driver are open (i.e., the eye opening degree). For example, the driver monitor ECU 2 extracts the outline of the upper eyelid and the outline of the lower eyelid for both the left and right eyes of the driver in the second image P2. The upper and lower eyelids of the left and right eyes can be detected using any of various pattern matching methods that use a template of the upper and lower eyelids set beforehand, for example. Then the driver monitor ECU 2 calculates the distance between the upper and lower eyelids for each eye as the eye opening degree of each eye.

Also, the driver monitor ECU 2 calculates the direction in which the driver is gazing (i.e., the direction of gaze). For example, the driver monitor ECU 2 extracts the position of the irises of the left and right eyes of the driver in the second image P2. The irises of the left and right eyes can be detected using an elliptic filter, for example. Typically, the shapes of the irises are often partially obstructed by the eyelids or the face being turned and so appear elliptical instead of round in the image. Therefore, a plurality of elliptic filters of different sizes are applied to both the left and right eyes of the driver in the second image P2 to obtain the brightness in the inner region as well as the outer region of the elliptical filter. If there is a difference between the brightness of the outer region and the brightness of the inner region at this time, the inner area of the elliptic filter is determined to be the iris and the position of the iris is obtained from the position of the elliptical filter used. Incidentally, detection of the position of the irises of the left and right eyes is not limited to this method. Other detection methods may be used, such as any of various pattern matching methods that use a template image of the iris set beforehand, or a method that extracts the position of a black region by binarizing the insides of the left and right eyes.

Then the driver monitor ECU 2 calculates the direction of gaze of the driver based on the position of the iris in both the left and right eyes of the driver, and the face direction α stored as the face direction detection data De. For example, the driver monitor ECU 2 calculates the angle of gaze of the driver with respect to the front of the vehicle as the direction of gaze. Then the driver monitor ECU 2 updates the eye opening degree/gaze detection data Dg using the data indicative of the calculated eye opening degrees and the data indicative of the direction of gaze.

In this way, the eye opening degree/gaze detection processing performed in step S56 described above is performed using the second image P2. In this case, contrast with respect to the portions that would appear dark with a typical exposure is able to be obtained so this second image P2 is suitable for image processing with respect to parts of the face such as the eyes of the driver. In this eye opening degree/gaze detection processing, the eyelids and irises in the image are searched for and the distances between the eyelids as well as the position of the irises and the like are extracted. As a result, accurate parameters can be extracted using the second image P2.

After the eye opening degree/gaze detection processing performed in step S56, the driver monitor ECU 2 outputs the processing results to the driver support system ECU 3 in step S57 and then proceeds on to the next step. More specifically, the driver monitor ECU 2 outputs the data indicative of the face angle α stored as the face direction detection data De and the data indicative of the eye opening degree and the gaze direction stored as the eye opening degree/gaze detection data Dg to the driver support system ECU 3. The driver support system ECU 3 the appropriately adjusts the characteristics of the occupant protection apparatus provided in the car, operates the collision avoidance/mitigation system, and issues an appropriate alarm to the driver, based on the data received from the driver monitor ECU 2 and the recognition results with respect to a vehicle or obstacle around the vehicle which are output from the millimeter-wave radar 4.

Next in step S58, the driver monitor ECU 2 corrects the electronic shutter time of the CCD 11 based on the first image P1 and the second image P2, and then proceeds on to the next step. More specifically, the driver monitor ECU 2 corrects the electronic shutter time for the first image P1 referencing the first image P1 stored as the first image data Da so that the brightness of the overall object captured in the first image P1 (typically, the brightness of the entire face of the driver in the image) is appropriate. Then the driver monitor ECU 2 updates the first electronic shutter data Dc using the corrected electronic shutter time. Also, the driver monitor ECU 2 corrects the electronic shutter time for the second image P2 referencing the second image P2 stored as the second image data Db so that the brightness of the overall object captured in the second image P2 (typically, the portion around the eyes of the driver in the image, e.g., the left and right eye search ranges) is appropriate. The driver monitor ECU 2 then updates the second electronic shutter data Dd using the corrected electronic shutter time.

Next, the driver monitor ECU 2 determines in step S59 whether the routine will end. For example, when the driver of the vehicle performs an operation to end the routine (such as turn the ignition switch off), the driver monitor ECU 2 determines that the routine will end. If the routine is to continue, the driver monitor ECU 2 returns to step S52 and repeats the process. On the other hand, it the routine is to end, the routine according to the flowchart ends.

In this way, with the driver imaging apparatus according to this example embodiment, image processing is performed using the portions where suitable contrast is obtained in two images with different exposures during imaging, so the state of the driver is able to be accurately determined. More specifically, image processing is performed for the wide portions (the outline, the nostrils, and the like) of the face of the driver that normally appear light using the first image P1 (i.e., the image with a relatively low exposure), while image processing is performed for parts (such as around the eyes) of the face of the driver that normally appear dark using the second image P2 (i.e., the image with a relatively high exposure). That is, the driver imaging apparatus described above makes a determination (regarding inattentiveness) based on the direction in which the face of the driver is pointing using the first image P1 with a relatively low exposure, and makes a determination (regarding the degree to which the eyes are open and the direction of gaze) based on the state of the eyes using the second image P2 with a relatively high exposure. As a result, the state of the driver can be accurately determined.

Incidentally, in the example embodiment described above, an example is described in which the CCD 11 captures images with different electronic shutter times in order to obtain the first image P1 and the second image P2 with different exposures. However, images with different exposures may also be obtained by adjusting other imaging parameters of the CCD 11. For example, images with different exposures may also be captured by adjusting the gain (i.e., sensitivity) of the CCD 11 for each image. Alternatively, images with different exposures may also be captured by adjusting the mechanical aperture in the driver monitor camera 1 for each image.

Also, in the description above, both the direction in which the driver is facing and the eye search range are detected using the first image P1 with a relatively low exposure. However, only one of these need be detected. Furthermore, in the foregoing description, both the eye opening degree and the direction of gaze of the driver are determined using the second image P2 with relatively large exposure. However, only one of these need be detected.

Moreover, in the description above, the state of the eyes of the driver is determined using the second image P2 with a relatively high exposure. Alternatively, however, the state of another part of the face of the driver may be determined instead using the second image P2. For example, that state of the mouth, eyebrows, and wrinkles and the like may be determined instead using the second image P2. In this invention, in addition to the image processing using the image in which the overall face is sure to be bright, accurate image processing of parts of the face is also possible by performing image processing using an image in which parts of the face are sure to be bright. Therefore, an image focusing on the brightness of a part of the face of the driver other than the eyes may also be used.

Also, with the order of the processes described above, a combination of two images captured with an extremely short interval in between is obtained by performing the step to obtain the first image P1 (i.e., step S52) and the step to obtain the second image P2 (i.e., step S53) in succession, then waiting until the image processing for each of those images is complete, and again performing the steps to obtain the first image P1 and the second image P2 in succession. Therefore, image processing in which it is assumed that the position and state of the object captured in both images is substantially the same is possible. However, when this kind of effect is not required, the first image P1 and the second image P2 may also be captured at another processing cycle. For example, the first image data Da and the second image data Db may be updated as needed using the first image P1 and the second image P2 captured alternately at an imaging cycle of the driver monitor camera 1 that is independent of the image processing cycle described above. In this case, the time interval between the timing at which the first image P1 used in steps S54 and S55 is captured and the timing at which the second image P2 used in step S56 is captured may be long, but there is also the advantage that the image processing of each image can be performed using the most recent image.

Also, in the example embodiment described above, the driver monitor camera 1 is arranged on the steering column 92, but it may be arranged in another position instead. That is, the driver monitor camera 1 may be arranged in any position as long as it enables the driver monitor camera 1 to capture an image of the face of the driver in the vehicle. For example, the driver monitor camera 1 may be arranged in an instrument panel in front of the driver, on the instrument panel, in the steering wheel, on an upper portion inside the vehicle cabin or the like.

In the example embodiment described above, the first image P1 and the second image P2 are used in image processing, but the number of images is not limited to two. The effect of this example embodiment can also be obtained when image processing is performed from a plurality of images.

The driver imaging apparatus and driver imaging method according to the invention are able to determine the state of the driver by capturing an image suitable for determining the state of the driver, and are thus useful in a system that determines the state of a driver seated in a vehicle, for example.

While the invention has been described with reference to example embodiments thereof, it is to be understood that the invention is not limited to the described embodiments or constructions. To the contrary, the invention is intended to cover various modifications and equivalent arrangements. In addition, while the various elements of the disclosed invention are shown in various example combinations and configurations, other combinations and configurations, including more, less or only a single element, are also within the scope of the appended claims.

The invention claimed is:

1. A driver imaging apparatus comprising:
an imaging unit that captures an image of a face of a driver of a vehicle;
a first image processing unit that performs image processing on a wide portion of the face of the driver in a first image captured by the imaging unit, using the first image; and
a second image processing unit that performs image processing on only a part less than the whole of the face of the driver in a second image captured by the imaging unit at a higher exposure than the exposure of the first image captured by the imaging unit, using the second image.

2. The driver imaging apparatus according to claim 1, wherein the second image processing unit detects at least one of i) the degree to which the eyes of the driver are open and ii) the direction in which the driver is gazing, by performing image processing on a portion around the eyes of the driver in the second image.

3. The driver imaging apparatus according to claim 1, wherein the second image processing unit detects at least one of i) the degree to which the eyes of the driver are open and ii) the direction in which the driver is gazing, by performing image processing on the mouth, eyebrows, and wrinkles of the driver in the second image.

4. The driver imaging apparatus according to claim 1, wherein the first image processing unit detects at least one of i) the direction in which the face of the driver is pointed with the front of the vehicle as a reference and ii) the position of the eyes of the driver, by performing image processing on the wide portion of the face of the driver in the first image.

5. The driver imaging apparatus according to claim 2, wherein:
the first image processing unit detects an area where the eyes of the driver are in the first image, by performing image processing on the wide portion of the face of the driver in the first image; and
the second image processing unit detects at least one of i) the degree to which the eyes of the driver are open and ii) the direction in which the driver is gazing, by performing image processing on the second image in the area detected by the first image processing unit.

6. The driver imaging apparatus according to claim 1, further comprising a shutter controlling unit that controls a shutter time which is the period of time during which light is taken in while the imaging unit is capturing an image,
wherein the shutter controlling unit controls the exposure when the imaging unit captures an image by making the shutter time when the second image is captured relatively long compared to the shutter time when the first image is captured.

7. The driver imaging apparatus according to claim 6, wherein the shutter controlling unit includes a shutter time correcting unit that corrects the shutter time when the first image is captured according to the brightness of the wide portion in the first image, and correcting the shutter time when the second image is captured according to the brightness of the part in the second image.

8. The driver imaging apparatus according to claim 1, further comprising an aperture controlling unit that controls the opening amount of an aperture that allows light into the imaging unit,
wherein the aperture controlling unit controls the exposure when the imaging unit captures an image by making the opening amount of the aperture when the second image is captured relatively large compared to the opening amount of the aperture when the first image is captured.

9. The driver imaging apparatus according to claim 8, wherein the aperture controlling unit includes an aperture opening amount correcting unit that corrects the opening amount of the aperture when the first image is captured according to the brightness of the wide portion in the first image, and correcting the opening amount of the aperture when the second image is captured according to the brightness of the part in the second image.

10. The driver imaging apparatus according to claim 1, further comprising a photosensitivity controlling unit that controls the photosensitivity of the imaging unit,
wherein the photosensitivity controlling unit controls the exposure when the imaging unit captures an image by making the photosensitivity when the second image is captured higher than the photosensitivity when the first image is captured.

11. The driver imaging apparatus according to claim 10, wherein the photosensitivity controlling unit includes a photosensitivity correcting unit that corrects the photosensitivity when the first image is captured according to the brightness of the wide portion in the first image, and correcting the photosensitivity when the second image is captured according to the brightness of the part in the second image.

12. The driver imaging apparatus according to claim 1, further comprising an exposure controlling unit that controls the exposures when the imaging unit captures the images,
wherein the exposure controlling unit cyclically alternates the timing at which the imaging unit captures an image with the exposure at which the first image is captured with the timing at which the imaging unit captures an image with the exposure at which the second image is captured.

13. The driver imaging apparatus according to claim 12, wherein the first image processing by the first image processing unit is performed at a separate timing than the second image processing by the second image processing unit.

14. The driver imaging apparatus according to claim 1, further comprising a storing unit that stores the first image and the second image,
wherein the first image processing unit and the second image processing unit each perform image processing using a combination of the first image and the second image captured in succession and stored in the storing unit.

15. The driver imaging apparatus according to claim 2, wherein the position of the eyes of the driver is identified by detecting the position of the nose of the driver.

16. A driver imaging apparatus comprising:
an imaging unit that captures an image of a face of a driver of a vehicle;
a face direction determining unit that determines the direction in which the face of the driver is pointed in a first image captured by the imaging unit with the front of the vehicle as a reference, using the first image; and
an eye information detecting unit that i) determines the degree to which the eyes of the driver are open in a second image, which is captured by the imaging unit at a higher exposure than the exposure of the first image captured by the imaging unit, using the second image, or ii) determines the direction in which the driver is gazing in the second image, which is captured by the imaging unit at a higher exposure than the exposure of the first image captured by the imaging unit, using the second image.

17. A driver imaging method comprising:
performing image processing on a wide portion of a face of a driver of a vehicle in a first image, in which the face of the driver is captured, using the first image; and
performing image processing on only a part less than the whole of the face of the driver in a second image, in which the face of the driver is captured at a higher exposure than the exposure of the first image, using the second image.

18. A driver imaging method comprising:
determining a direction in which a face of a driver of a vehicle is pointed in a first image, in which the face of the driver is captured, with the front of the vehicle as a reference, using the first image; and
determining a degree to which the eyes of the driver are open in a second image, in which the face of the driver is captured at a higher exposure than the exposure of the first image, using the second image, or determining a direction in which the driver is gazing in the second image, in which the face of the driver is captured at a higher exposure than the exposure of the first image, using the second image.

19. The driver imaging apparatus according to claim 4, wherein the position of the eyes of the driver is identified by detecting the position of the nose of the driver.

20. The driver imaging apparatus according to claim 1, wherein the part of the face of the driver is an area of the face of the driver different than the wide portion of the face of the driver.

21. The driver imaging apparatus according to claim 1, wherein the second image processing unit detects the direction in which the driver is gazing, by performing image processing on a portion around the eyes of the driver in the second image.

* * * * *